United States Patent [19]

Houminer et al.

[11] 4,259,969
[45] Apr. 7, 1981

[54] SMOKING COMPOSITIONS

[75] Inventors: Yoram Houminer; Edward B. Sanders, both of Richmond, Va.

[73] Assignee: Philip Morris Incorporated, New York, N.Y.

[21] Appl. No.: 8,013

[22] Filed: Jan. 31, 1979

[51] Int. Cl.³ .............................................. A24B 15/38
[52] U.S. Cl. ..................................... 131/278; 131/144
[58] Field of Search .................. 131/17 R, 140 B, 144

[56] References Cited

U.S. PATENT DOCUMENTS 3,914,227 10/1975 Pittet et al. .......................... 131/144
3,917,872 11/1975 Winter et a. ........................ 131/17 R

FOREIGN PATENT DOCUMENTS 2060363 6/1971 France .................... 131/17 R

OTHER PUBLICATIONS

Chem. Abst., vol. 90, No. 3, 15th Jan., 1979, p. 329, no. 19276Z.

Primary Examiner—V. Millin
Attorney, Agent, or Firm—Susan A. Hutcheson; Arthur I. Palmer, Jr.

[57] ABSTRACT

This invention provides tobacco and non-tobacco smoking compositions which contain a substituted-heterocyclic compound as a flavorant additive.

In one of its embodiments this invention provides tobacco compositions which contain a substituted-pyrazine flavorant additive such as 2,3-dihydroxy-2,3-dimethyl-1,4-bis(3,5,6-trimethyl-2-pyrazinyl)butane:

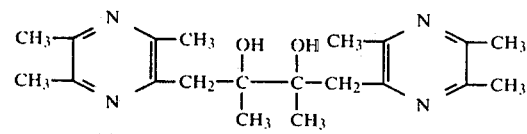

Under smoking conditions the above illustrated substituted-pyrazine additive and its pyrolysis products flavor the mainstream and sidestream smoke.

25 Claims, No Drawings

SMOKING COMPOSITIONS

BACKGROUND OF THE INVENTION

There has been increasing interest in substances which can function as flavoring agents for modifying or improving the flavor and aroma of foodstuffs, tobaccos, beverages and pharmaceutical preparations.

The role of alkylpyrazines and alkylpyridines as natural flavor constituents in various foodstuffs is well known. This knowledge has stimulated the development of foodstuff formulations containing synthetic alkylpyrazines and alkylpyridines as flavorant additives.

U.S. Pat. No. 3,328,402 discloses pyrazine derivatives corresponding to the formula:

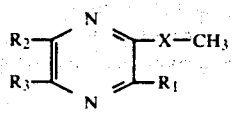

wherein X represents a member selected from the group consisting of oxygen and sulfur and one of the symbols $R_1$, $R_2$ and $R_3$ represents a methyl radical, the other two representing hydrogen. This class of pyrazine derivative imparts a flavor and aroma of roasted hazelnuts, peanuts or almonds when incorporated in foodstuffs and beverages as a flavorant additive.

U.S. Pat. No. 3,619,210 describes the use of 2,6-dimethylpyrazine as a flavor enhancer in chocolate preparations. U.S. Pat. No. 3,829,582 discloses that pyrazine derivatives are useful for imparting fatty-fried flavor to potato chips.

More recently, it has been established that alkylpyrazines are natural components of tobacco smoke, and that they most probably are important contributors to tobacco smoke flavor [A. Baggett et al, *J. Chromatog,* 97, 79 (1974)]. Further, it has been disclosed in the patent literature that addition of alkylpyrazines to tobacco results in an improvement in the flavor of smoking compositions as perceived by a test panel.

British Pat. No. 1,244,068 describes a method for influencing the smoke flavor of tobacco or a tobacco mixture which consists of treating the tobacco with a pyrazine derivative of the following chemical structure:

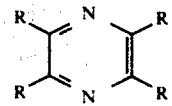

in which each R is independently a hydrogen atom, an aliphatic radical, an alicyclic radical or an aromatic hydrocarbon radical, such radicals having up to 9 carbon atoms, or R is a heterocyclic radical containing 4 to 9 carbon atoms.

U.S. Pat. No. 3,402,051 describes a process for imparting a popcorn-like flavor and aroma to tobacco and foodstuffs by the incorporation of a 2-acetylpyrazine derivative therein.

Other patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 3,881,025.

Alkylpyridines have also been found to be useful tobacco additives. As an example, U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of both pyrazine and pyridine derivatives employed as tobacco flavorants in the prior art, as illustrated by the above described technical literature, that the respective heterocyclic derivatives have the disadvantage of both high volatility and low odor threshold. Both of these properties significantly restrict the extent that these heterocyclic derivatives can be utilized as flavorants in tobacco compositions. A quantity of a pyrazine or pyridine derivative in a tobacco composition sufficient to have a noticeable effect in low delivery cigarettes causes a marked pack aroma.

Accordingly, it is a main object of this invention to provide tobacco and non-tobacco smoking compositions which have incorporated therein a substituted pyrazine or pyridine compound as a flavorant additive which is characterized by low volatility and low pack aroma.

It is another object of this invention to provide smoking compositions of tobacco and non-tobacco materials, and blends thereof, containing a substituted-pyrazine and/or substituted-pyridine flavorant additive, which smoking compositions are adapted to impart flavoring to the mainstream and sidestream smoke under smoking conditions.

It is a further object of this invention to provide novel hydroxyethyl-substituted pyrazine and pyridine compounds which can be subjected to pyrolysis conditions to yield constituents which can enhance the flavor and aroma of smoking compositions and foodstuffs.

Other objects and advantages of the present invention shall become apparent from the accompanying description and examples.

DESCRIPTION OF THE INVENTION

One or more objects of the present invention are accomplished by the provision of a smoking composition which comprises an admixture of (1) combustible filler selected from natural tobacco, reconstituted tobacco and non-tobacco substitutes, and (2) between about 0.0005 and 2 weight percent, based on the total weight of filler, of a substituted heterocyclic compound corresponding to the formula:

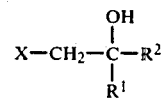

wherein X is selected from pyrazine and pyridine radicals corresponding to the chemical structures:

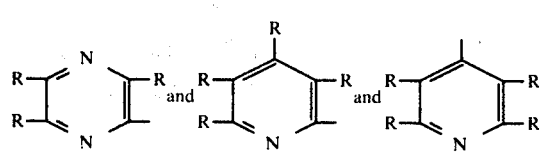

where R is a substituent selected from hydrogen and methyl; $R^1$ is a substituent selected from hydrogen and alkyl groups containing between 1 and about 10 carbon atoms; $R^2$ is a substituent selected from aliphatic, alicyclic and aromatic groups containing between 1 and about 12 carbon atoms, and any heteroatom present in the $R^2$ group is either oxygen or nitrogen; and $R^1$ and $R^2$ when taken together with connecting elements form an alicyclic structure.

Illustrative of the $R^1$ substituent in the formula represented above are alkyl groups such as methyl, ethyl, propyl, isobutyl, hexyl, octyl, isooctyl, decyl and the like. Illustrative of the $R^2$ substituent are groups which include methyl, propenyl, butyl, pentyl, hexenyl, 1-hydroxyethyl, methoxyethyl, acetyl, cyclopropyl, cyclobutyl, cyclopentyl, cyclohexyl, menthyl, furyl, tetrahydrofuryl, piperidyl, pyrrolidyl, pyrazolyl, phenyl, tolyl, xylyl, benzyl, phenylethyl, methoxyphenyl, naphthyl, pyridyl, pyridazyl, pyrimidyl, pyrazyl, and the like. The $R^1$ and $R^2$ groups when taken together with the connecting elements form an alicyclic group such as cyclopentyl, cyclohexyl, cycloheptyl, menthyl, and the like.

A preferred type of $R^2$ substituent is one selected from aliphatic, alicyclic and aromatic radicals containing between 1 and about 12 carbon atoms and 0-3 oxygen and/or nitrogen atoms. Illustrative of preferred $R^2$ substituents are alkyl; alkyl containing one or more oxygen atoms in the form of ketone, aldehyde, ether or alcohol functionality; phenyl; alkyl and alkoxyl substituted phenyl; pyrazine; alkyl substituted pyrazine; pyridine; alkyl substituted pyridine; and combinations of these radicals.

A substituted heterocyclic compound corresponding to the formula above is a low volatility flavorant which under normal smoking conditions, or other comparable intensively localized heating conditions, volatilizes and evolves as a gasiform component. Concomitantly, a portion of the substituted heterocyclic compound pyrolyzes into products which respectively also exhibit flavorant properties. These secondary flavorant compounds are released in accordance with the following illustrated reaction mechanisms:

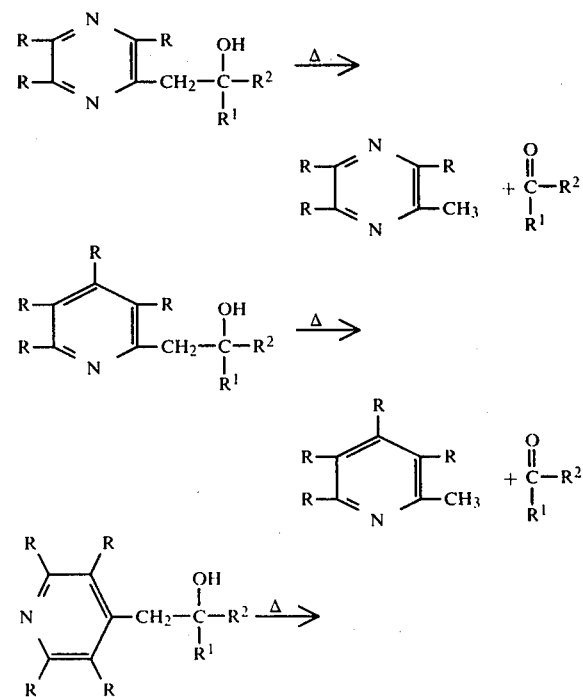

Each of the pyrolysis products illustrated above can impart flavor and aroma to tobacco and non-tobacco smoke under smoking conditions.

Preparation of Substituted-Pyrazine Compounds

A preferred method of preparing the novel substituted-pyrazine and substituted-pyridine compounds of the present invention is by the reaction of a methylpyrazine or methylpyridine derivative with a carbonyl derivative, both of which derivatives are appropriately substituted:

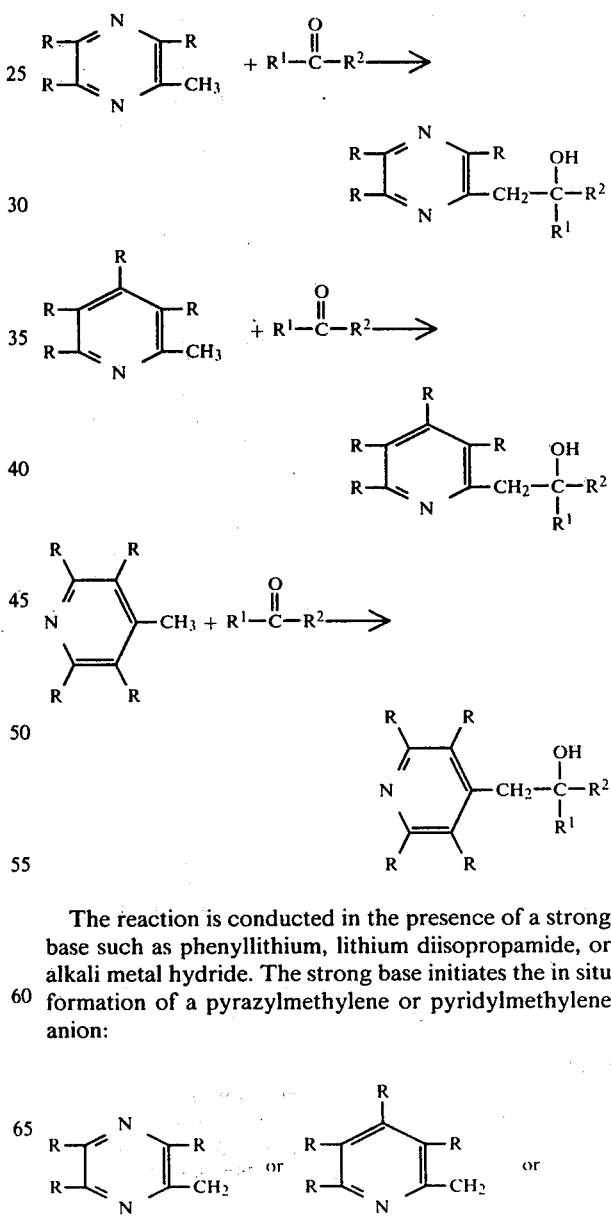

The reaction is conducted in the presence of a strong base such as phenyllithium, lithium diisopropamide, or alkali metal hydride. The strong base initiates the in situ formation of a pyrazylmethylene or pyridylmethylene anion:

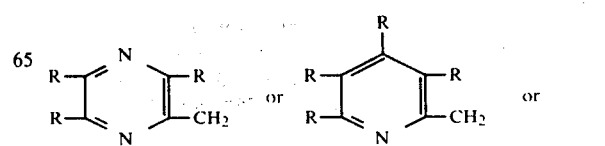

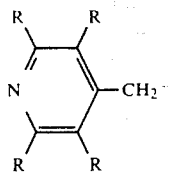

Preferably, the base is added to the pyrazine or pyridine starting material in an inert solvent medium maintained at a temperature between about 0° C. and 50° C. and under an inert atmosphere. This procedure is followed by the addition of the carbonyl compound to the reaction medium at a temperature between about −65° C. and 25° C. With few exceptions, the resultant hydroxyethyl-substituted pyrazine or pyridine addition product is an odorless, white crystalline solid.

Preparation of Tobacco Compositions

The present invention smoking compositions can be prepared by admixing natural tobacco and/or reconstituted tobacco and/or a non-tobacco substitute with between about 0.0005 and 2 weight percent based on the weight of the smoking composition, of a flavorant additive which corresponds to the structural formulae set forth hereinabove in definition of the hydroxyethyl-substituted pyrazine and pyridine compounds.

The substituted-pyrazine or substituted-pyridine flavorant additive can be incorporated into the tobacco in accordance with methods known and used in the art. Preferably the flavorant additive is dissolved in a solvent such as water, alcohol, or mixtures thereof, and then sprayed or injected into the tobacco or non-tobacco substitute matrix. Such method ensures an even distribution of the flavorant additive throughout the tobacco, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or non-tobacco substitute filler in a concentration between about 2-20 weight percent, based on the weight of filler, and then subsequently to blend the treated filler with filler which does not contain flavorant additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein; incorporated herein by reference.

Illustratively, U.S. Pat. No. 3,529,602 describes a burnable sheet which may be used as a tobacco substitute, which sheet contains ingredients which include (1) a film-forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or a clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formations of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smokable material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

In another embodiment, the present invention also contemplates the incorporation of one of the substituted heterocyclic compounds described above into an article of manufacture which is burned under controlled conditions within the environment of a human habitat. In particular, the combustible articles contemplated are those such as candles, room deodorizers, manufactured fireplace fuel, and the like, the burning of which evolves a gasiform effluent which can be sensed by individuals within olfactory proximity. As it is apparent, wood logs can also be treated with a solution of a substituted heterocyclic compound prior to ignition in a fireplace.

The incorporation of between about 0.01 and 10 weight percent of a novel substituted-pyrazine or substituted-pyridine compound of the present invention into a candle, for example, can introduce a pleasant aroma or fragrance into a confined living space when the candle is lighted.

In a further embodiment, the present invention provides a method for improving the flavor of a foodstuff (e.g., a meat-containing or meat-simulating product) which comprises contacting the foodstuff with a non-toxic gasiform effluent which is generated by the burning of a combustible material (e.g., a solid fuel) having admixed therewith between about 0.01 and 10 weight percent, based on the weight of combustible content, of a novel substituted heterocyclic compound of the present invention. Illustrative of one of the applications contemplated is the incorporation of the substituted heterocyclic compound in a smokehouse system for curing meats. Also, a substituted heterocyclic compound can be incorporated in manufactured carbonaceous fuels (e.g., charcoal briquettes) which are used for broiling raw meat and fish products.

As it is apparent, a present invention substituted heterocyclic compound can be employed with optimal advantage in any application for adding flavor or enhancing the flavor of a foodstuff in which the foodstuff is subjected to a cooking cycle. The substituted heterocyclic compound can be admixed with or applied to the surface of foodstuffs prior to or during the cooking phase. The substituted heterocyclic compound can be blended with edible solids or liquids to facilitate its application as a flavorant additive. A blend of between about 0.01 and 10 weight percent of substituted heterocyclic compound in vegetable oil, for example, is a convenient medium for imparting flavor to foodstuffs in deep-fry operations. The substituted heterocyclic compound can also be incorporated as a flavorant additive in prepared sauces, gravies and dressings. Suitable edible vehicles or carriers for a present invention substituted heterocyclic compound include fats and oils such as cottonseed oil, soy bean oil, olive oil, and peanut oil; emulsified fats and oils such as butter and margarine; gums such as guar, locust bean, gum arabic, carrageenen; and the like.

The following examples are further illustrative of the present invention. The reactants and other specific ingredients are presented as being typical, and various modifications can be derived in view of the foregoing disclosure within the scope of the invention.

EXAMPLE I

Preparation Of
2-(2-Hydroxy-2-phenylethyl)-3,5,6-trimethylpyrazine

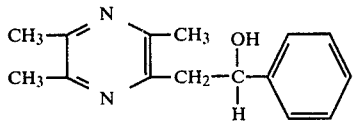

A solution of phenyllithium in benzene-ether (90 milliliters, 0.095 mole) was diluted with 100 milliliters anhydrous ether and cooled to 0° C. A solution of 13.6 grams tetramethylpyrazine (0.1 mole) in 50 milliliters ether was added slowly to the phenyllithium solution. The reaction mixture was stirred at room temperature for 2 hours and heated under reflux for 1 hour. The mixture was allowed to cool to room temperature and a solution of 10 grams of freshly distilled benzaldehyde (0.1 mole) in 50 milliliters of ether was added dropwise. The mixture was stirred at room temperature for an additional 1.5 hours and cooled to 0° C. Water was added, and the organic phase was separated and washed three times with water. The recovered water extracts were washed with methylene chloride.

The organic layers were combined and dried over sodium sulfate and sodium carbonate. The solvent was removed under reduced pressure, and 50 milliliters of ether were added to precipitate a white solid. The solid was collected by filtration and washed with three 20 milliliter portions of ether. The yield of product was 11.5 grams, m.p. 126°–127° C. [lit. m.p., 126°–127° C., S. K. Chakrabarthy and R. Levine, *J. Heterocycl. Chem.*, 3, 265 (1966)]. An additional 0.6 gram of product was obtained from ether solution, m.p. 125°–127° C., for a total yield of 54%.

EXAMPLE II

Preparation Of
2-(2-Hydroxy-2-p-methylphenylethyl)-3,5,6-trimethylpyrazine

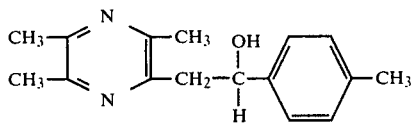

To a solution of phenyllithium in 150 milliliters 7:3 benzene-ether (0.1 mole) at 0° C. was slowly added a solution of 13.6 grams of tetramethylpyrazine (0.1 mole). The mixture was stirred at room temperature for 2 hours and heated under reflux for 1.5 hours. The mixture was cooled to 0° C., and a solution of 12.0 grams of p-tolualdehyde (0.1 mole) in 50 milliliters of ether was added dropwise. The reaction mixture was stirred at room temperature for 1 hour and then treated in the manner of Example I. The crude product was crystallized from ether to yield 10.7 grams of product (42%) as fine white needles, m.p. 99°–101° C.

Analysis Calculated for $C_{16}H_{20}N_2O$: C,74.96; H,7.86; N,10.03. Found: 75.19; 7.96; 10.88.

EXAMPLE III

Preparation Of
2-(2-Hydroxy-2-p-methoxyphenylethyl)-3,5,6-trimethylpyrazine

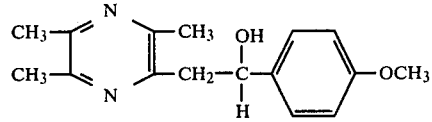

The reaction of 13.6 grams (0.1 mole) of tetramethylpyrazine with 13.6 grams (0.1 mole) of p-anisaldehyde was conducted in the manner described in Example II. Crystallization of the recovered crude product from ether yielded 14.2 gram (52%) of white crystals, m.p. 97°–98° C.

Analysis Calculated for $C_{16}H_{20}N_2O_2$: C,70.56; H,7.40; N,10.28. Found: 70.33; 7.60; 10.19.

EXAMPLE IV

Preparation Of
2-[2-Hydroxy-2-(2-furyl)ethyl]-3,5,6-trimethylpyrazine

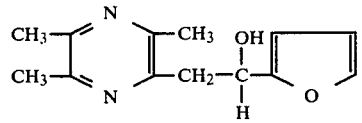

The reaction of 13.6 grams (0.1 mole) of tetramethylpyrazine with 9.6 grams (0.1 mole) of furfural was performed in the manner described in Example II. A crude oily product was recovered which was contaminated with unreacted tetramethylpyrazine and two side products. Addition of water to the oil resulted in formation of crystals which were identified as a mixture of starting material and one of the side products. The crystals were removed by filtration, and washed with water. The filtrate mixture of oil and water was acidified, and washed with ether, neutralized and extracted with methylene chloride.

The methylene chloride extracts were combined and dried over sodium sulfate. Evaporation of the solvent gave 6.7 grams of an oil which was primarily the desired product. The oil was chromatographed on 230 grams of silica gel to give 5.3 grams of an oil which solidified on standing. Recrystallization of the solid from hexane-ether (1:1) yielded 4.5 grams (22%) of product as fine needles, m.p. 69°–71° C.

Analysis Calculated for $C_{13}H_{16}N_2O_2$: C,67.22; H,6.94; N,12.06. Found: 67.47; 6.86; 12.16.

EXAMPLE V

Preparation Of
2-(2-Hydroxy-4-methylpentyl)-3,5,6-trimethylpyrazine

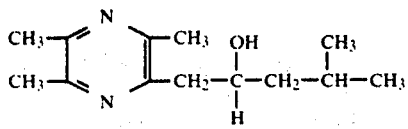

The reaction of 13.6 grams (0.1 mole) of tetramethylpyrazine with 8.6 grams (0.1 mole) isovaleraldehyde was carried out in the manner described in Example II. The crude reaction mixture was washed with 50 milliliters of 6 N HCl, and the aqueous layer was separated and washed with two 50 milliliter portions of methylene chloride. The acidic solution was neutralized with sodium carbonate and the oil that separated was dissolved in methylene chloride. The organic solution was dried over sodium sulfate, and the solvent was evaporated to give 13.5 grams of an oil. Distillation of the oil yielded 7.7 grams (35%) of product, b.p. 98°-100° C./0.05 mm Hg.

Analysis Calculated for $C_{13}H_{22}N_2O$: C,70.23; H,9.97; N,12.60. Found: 70.37; 9.86; 12.50.

EXAMPLE VI

Preparation Of
2-(2-Hydroxy-2-methyl-3-oxobutyl)-3,5,6-trimethylpyrazine (Product A) And
2,3-dihydroxy-2,3-dimethyl-1,4-bis(3,5,6-trimethyl-2-pyrazyl)butane (Product B)

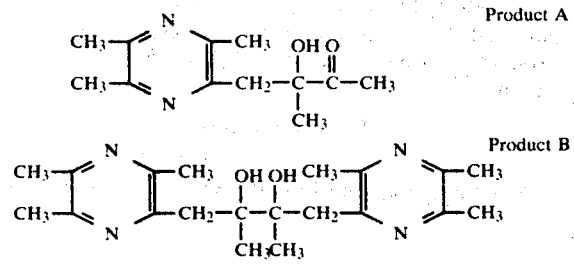

Lithium diisopropylamide (0.1 mole) was prepared by reacting 0.1 mole butyllithium with 10.1 grams (0.1 mole) diisopropylamine in 50 milliliters of ether at 0° C. To the etheral solution was added 13.6 grams (0.1 mole) of tetramethylpyrazine in 80 milliliters of ether, and the resulting reaction mixture was stirred for 2 hours at 0° C. The solution was cooled to −65° C. employing a dry ice-acetone bath, and a solution of 8.6 grams (0.1 mole) of biacetyl in 20 milliliters of ether was added rapidly. Stirring was continued for 30 minutes at −65° C., after which water was added. The organic layer was separated, washed with water, and dried over magnesium sulfate. Removal of the solvent and chromatography of the crude product on 300 grams silica gel with hexane-acetone yielded 5.2 grams (24%) of Product A, m.p. 75°-77° C., and 4.8 grams (27%) of Product B, m.p. 119°-123° C.

For Product A:
Analysis Calculated for $C_{12}H_{18}N_2O_2$: C,64.84; H,8.16; N,12.60. Found: 64.81; 8.14; 12.55.

For Product B:
Analysis Calculated for $C_{20}H_{30}N_4O_2$: C,67.01; H,8.44; N,15.63. Found: 67.11; 8.59; 15.71.

EXAMPLE VII

Preparation of
2-(2-Hydroxy-2-p-methoxyphenylethyl)-6-methylpyrazine

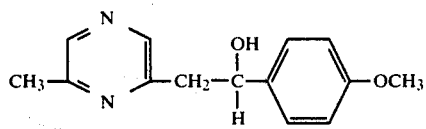

A solution of 5.05 grams (50 mmole) of diisopropylamine in 40 milliliters of ether was added to 47.1 mole butyllithium in hexane at 0° C. After stirring the resulting solution for 15 minutes, 5.4 grams (50 mmole) of 2,6-dimethylpyrazine in 50 milliliters of ether were added slowly and the reaction mixture was stirred at 0° C. for 30 minutes. A solution of 5.4 grams (40 mmole) of p-methoxybenzaldehyde in 40 milliliters of ether was added, and stirring at 0° C. was continued for an additional 30 minutes. Water was added, the organic phase was separated, washed with water and dried over magnesium sulfate.

Evaporation of the solvent at reduced pressure gave 9.5 grams of an amorphous solid. Two recrystallizations from ether gave 1.0 grams of fine needles, m.p. 90°-92° C. The remaining material was chromatographed on silica gel employing hexane-acetone to give 6.0 grams of a product, which was recrystallized to yield 5.2 grams of product, m.p. 90°-92° C. Total yield from the reaction was 6.2 grams (63%).

Analysis Calculated for $C_{14}H_{16}N_2O_2$: C,68.82; H,6.60; N,11.47. Found: 68.84; 6.70; 11.54.

EXAMPLE VIII

Preparation of
2-(2-Hydroxy-2-p-methoxyphenylethyl)-3-methylpyrazine

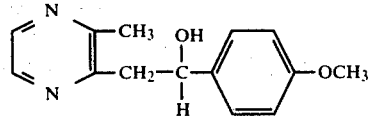

The preparation was conducted in the manner described in Example VII, using 5.05 grams (50 mmole) of diisopropylamine in 40 milliliters of ether, 47.1 mmole of butyllithium, and 5.4 grams (50 mmole) of 2,3-diemthylpyrazine in 50 milliliters of ether. The crude product (10.8 grams) was chromatographed on 250 grams silica gel using hexane-acetone to give 5.9 grams (48%) of a pure solid. Recrystallization from ether yielded plates, m.p. 89°-91° C.

Analysis Calculated for $C_{14}H_{16}N_2O_2$: C,68.82; H,6.60; N,11.47. Found: 69.00; 6.71; 11.58.

EXAMPLE IX

Preparation of 2-(2-Hydroxy-2-p-methoxyphenylethyl)-5-methylpyrazine

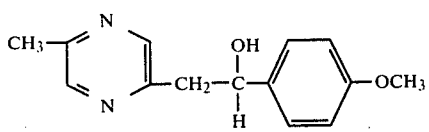

The preparation was carried out as described above for Example VII, using 10.10 grams (100 mmole) of diisopropylamine in 100 milliliters of ether, 94.6 mmole of butyllithium, and 10.7 grams (100 mmole) of 2,5-dimethylpyrazine in 100 milliliters of ether. The crude product was found to be a complex mixture. Preparative thin layer chromatography was conducted on the crude product to give 1.30 grams (10.5%) of a solid. Recrystallization of the solid from ether yielded 260 mg (2%) of product, m.p. 110°–113° C.

Analysis Calculated for $C_{14}H_{16}N_2O_2$: C,68.82; H,6.60; N,11.47. Found: 69.01; 6.71; 11.37.

EXAMPLE X

Preparation of 2,3-Dihydroxy-2,3-dimethyl-1-(3,5,6-trimethyl-2-pyrazyl)-4-(6-methyl-2-pyrazyl)butane

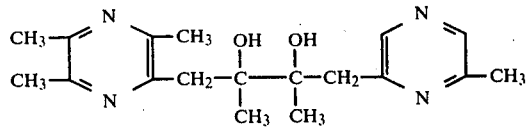

A solution of 2.0 grams (20 mmole) of diisopropylamine in 40 milliliters of ether was treated at 0° C., with 20 mmole butyllithium in 9 ml of hexane, and the mixture was stirred at 0° C. for 15 minutes. A solution of 2.16 grams (20 mmole) of 2,6-dimethylpyrazine in 50 milliliters of ether was added at 0° C., and the resulting mixture was stirred for 20 minutes. A solution of 2-(2-hydroxy-2-methyl-3-oxobutyl)-3,5,6-trimethylpyrazine (2.0 grams, 9 mmole) in 60 milliliters of ether was added to the reaction mixture at 0° C. The mixture was stirred at room temperature for 1 hour, then a small amount of water was added, the organic layer was separated and dried over magnesium sulfate. Evaporation of the solvent gave 1.6 grams of an oil. Preparative thin layer chromatography of 0.5 grams of the oil yielded 0.32 grams of a slightly yellow oil that was homogeneous on tlc.

Analysis Calculated for $C_{18}H_{26}N_4O_2$: C,65.42; H,7.93; N,16.96. Found: 65.32; 8.05; 16.69.

EXAMPLE XI

Preparation Of 1-Methyl-3-hydroxy-3-(3,5,6-trimethyl-2-pyrazyl)methyl-4-isopropylcyclohexane

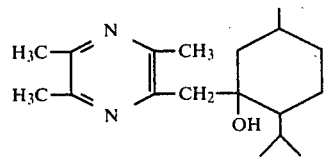

The preparation is conducted in the manner described in Example VII using 10.1 grams (0.1 mole) of diisopropylamine in 80 milliliters of ether, 0.95 mole of butyllithium, 13.6 grams (0.1 mole) of tetramethylpyrazine, and 15.4 grams (0.1 mole) of p-menthone. The product is isolated by chromatography on silica gel.

EXAMPLE XII

Preparation of 2-[2-Hydroxy-2-(2-pyrazyl)propyl]-3,5,6-trimethylpyrazine

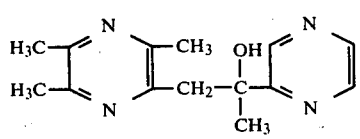

The preparation is conducted in the manner described in Example VII using 10.1 grams (0.1 mole) of diisopropylamine in 80 milliliters of ether, 0.95 mole of butyllithium, 13.6 grams (0.1 mole) of tetramethylpyrazine, and 12.2 grams (0.1 mole) of 2-acetylpyrazine. The product is isolated as before and purified by recrystallization.

EXAMPLE XIII

Preparation of 2-(2-Hydroxy-2-methylheptyl)-3,5,6-trimethylpyrazine

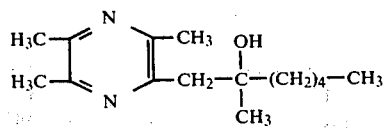

The preparation is carried out in the manner described in Example VII using 10.1 grams (0.1 mole) of diisopropylamine in 80 milliliters of ether, 0.95 mole of butyllithium, 13.6 grams (0.1 mole) of tetramethylpyrazine, and 12.8 grams (0.1 mole) of 2-heptanone. The reaction is worked up as before, and the product is isolated by chromatography on silica gel.

EXAMPLE XIV

Preparation of 2-(2-Hydroxy-2-phenylethyl)pyridine

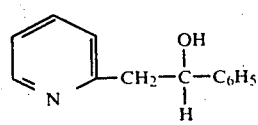

A solution of 4.65 grams (0.05 mole) of 2-picoline in 40 milliliters of ether was added, with stirring, to a solution of phenyllithium (0.05 mole) in 30 milliliters of benzene diluted with 50 milliliters of ether. The solution was refluxed for 1 hour and then cooled to 0° C.; a solution of 5.3 grams (0.05 mole) of benzaldehyde in 30 milliliters of ether was added slowly at 0° C. The reaction mixture was stirred at room temperature for 30 minutes. Water was added, and the organic layer was separated and washed with water. Methylene chloride (100 milliliters) was added; the solution was dried over magnesium sulfate and evaporated under reduced pressure to give a solid. The solid was stirred with 50 milliliters of ether, filtered, and washed with 20 milliliters of ether to give 4.1 grams (40%) of virtually pure product. Recrystallization from 1:1 hexane-acetone gave plates, m.p. 105°–107° C. (Lit. m.p., 110° C., Beyerman, H. C., W. Eveleens, and Y. M. F. Muller, *Rec. Trav. Chim.*, 75, 1956, p. 63).

Analysis Calculated for $C_{13}H_{13}NO$: C,78.36; H,6.58; N,7.03. Found: 78.56; 6.70; 7.04.

EXAMPLE XV

Preparation of 4-(2-Hydroxy-2-phenylethyl)pyridine

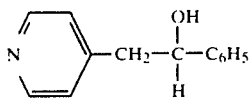

A solution of 8.8 grams (0.1 mole) of thiophene in 100 milliliters of ether at 0° C. was treated with a solution of butyllithium (0.1 mole) in 45 milliliters of hexane. The resulting solution was stirred for 2.5 hours at room temperature after which 9.3 grams (0.1 mole) of 4-picoline in 40 milliliters of ether was added. The reaction mixture was stirred for 19 hours and then cooled to 0° C. To the cooled solution was added 10.6 grams (0.1 mole) of benzaldehyde in 50 milliliters of ether; the mixture was stirred for 30 minutes at room temperature. Water was added, and the organic layer was separated and washed with water. The basic material was extracted into 10% hydrochloric acid. The acidic solution was washed with methylene chloride, neutralized with solid sodium carbonate, and the resulting oil was taken up in methylene chloride. The methylene chloride solution was washed with water, dried over magnesium sulfate, and evaporated to give 11.1 grams of an oil. Addition of about 50 milliliters of ether to the oil resulted in crystallization. The solid was collected and recrystallized from ether to give 3.1 grams (16%) of the pure product as fine needles, m.p. 108°–110° C.

Analysis Calculated for $C_{13}H_{13}NO$: C,78.36; H,6.58; N,7.03. Found 78.44; 6.71; 6.91.

EXAMPLE XVI

Preparation Of 2-(2-Hydroxy-2-p-methoxyphenylethyl)pyridine

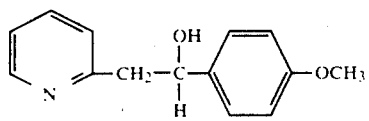

The preparation of 2-(2-hydroxy-2-p-methoxyphenylethyl)pyridine is carried out using the procedure described in Example XIV from 0.05 mole of phenyllithium, 4.65 grams (0.05 mole) of 2-picoline, and 6.8 grams (0.05 mole) of p-anisaldehyde. The product is crystallized from ether and recrystallized from acetone-hexane.

EXAMPLE XVII

Preparation of 2-(2-Hydroxy-2-phenylethyl)-6-methylpyridine

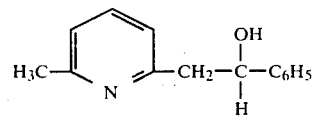

The preparation of 2-(2-hydroxy-2-phenylethyl)-6-methylpyridine is carried out using the procedure described in Example XIV from 0.05 mole of phenyllithium, 5.35 grams (0.05 mole) of 2,6-lutidine, and 5.3 grams (0.05 mole) of benzaldehyde. The product is crystallized from ether and recrystallized from acetone-hexane. [See J. Hebky and J. Stanek, *J. Chem. Listy*, 46, 562 (1952)].

EXAMPLE XVIII

Preparation Of Smoking Compositions Containing A Flavorant Compound

Cigarettes were fabricated using tobacco treated with 0.2% 2-(2-hydroxy-2-p-methylphenylethyl)-3,5,6-trimethylpyrazine and with 0.015% 2-(2-hydroxy-2-p-methoxyphenylethyl)-3,5,6-trimethylpyrazine. The cigarettes were targeted to deliver 5–6 mg tar per cigarette.

Untreated controls were prepared, and the treated cigarettes were compared to the controls by an experienced smoking panel. The treated cigarettes were found to have a distinct fruity note, more body and more response as compared to the controls.

EXAMPLE XIX

Preparation Of Smoking Compositions Containing A Flavorant Compound

Cigarettes were fabricated using tobacco treated with 0.015% 2-(2-hydroxy-2-phenylethyl-3,5,6-trimethylpyrazine and with 0.02% 2-(2-hydroxy-2-p-methoxyphenylethyl)-3,5,6-trimethylpyrazine. The cigarettes were targeted to deliver 5–6 mg tar per cigarette.

Untreated controls were prepared and the treated cigarettes were compared to the controls by an experienced smoking panel. The treated cigarettes were found to have a sweet note, more body and more response as compared to the controls.

EXAMPLE XX

Determination Of Differential Flavoring Of Mainstream And Sidestream Tobacco Smoke Cigarettes targeted to deliver 5–6 mg tar per cigarette were fabricated using tobacco treated with 0.046% (ea. 400 μg/cigt) 2-(2-hydroxy-2-phenylethyl)-3,5,6-trimethylpyrazine as a flavorant additive. The cigarettes were machine smoked under controlled laboratory conditions and gas chromatographic analyses of flavorant additive, benzaldehyde and tetramethylpyrazine were performed on mainstream smoke, sidestream smoke and the filter.

The data obtained are presented in table form below. Total accountability of the flavorant additive was 95% based on 0.76 gram of tobacco per cigarette actually smoked.

TABLE

Analytical Determination Of Flavorant Additive And Its Pyrolysis Products On Smoking

| Compound | Amt. in MS/Cigt. | Amt. in SS/Cigt. | Amt. in Filter |
| --- | --- | --- | --- |
| Flavorant Additive | 26 μg (0) | 58 μg (0) | 52 μg (0) |
| Benzaldehyde | 17 μg (13) | 169 μg (98) | 3 μg (0) |
| Tetramethylpyrazine | 12 μg (8) | 159 μg (76) | 26 μg (1) |

Amounts in parentheses are those values determined in an untreated control cigarette. A conventional cellulose acetate filter (21 mm length) was employed in the cigarettes (85 mm) each of which contained 0.85 gram of tobacco.

The comparative data indicate that under cigarette smoking conditions the pyrolysis products from the 2-(2-hydroxy-2phenylethyl)-3,5,6-trimethylpyrazine flavorant additive were substantially present in the sidestream smoke thereby differentially imparting flavor and aroma to the sidestream cigarette smoke.

What is claimed is:

1. A smoking composition comprising an admixture of (1) combustible filter selected from the group consisting of natural tobacco, reconstituted tobacco and non-tobacco substitutes, and (2) between about 0.0005 and 2 weight percent, based on the total weight of filter, of a substituted heterocyclic compound corresponding to the formula:

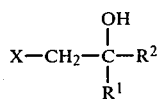

wherein X is selected from pyrazine and pyridine radicals corresponding to the chemical structures:

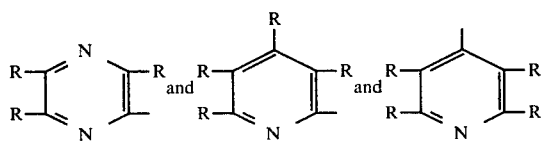

where R is a substituent selected from hydrogen and methyl; $R^1$ is a substituent selected from hydrogen and alkyl groups containing between 1 and about 10 carbon atoms; $R^2$ is a substituent selected from aliphatic, alicyclic and aromatic groups containing between 1 and about 12 carbon atoms, and any heteroatom present in the $R^2$ group is either oxygen or nitrogen; and $R^1$ and $R^2$ when taken together with connecting elements form an alicyclic structure.

2. A smoking composition in accordance with claim 1 wherein the non-tobacco substitutes are selected from pectinaceous, cellulosic and carbohydrate materials.

3. A smoking composition comprising an admixture of (1) combustible filler selected the group consisting of natural tobacco, reconstituted tobacco and non-tobacco substitutes, and (2) between about 0.0005 and 2 weight percent, based on the total weight of filler, of a substituted-pyrazine compound corresponding to the formula:

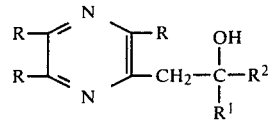

wherein R is a substituent selected from hydrogen and methyl; $R^1$ is a substituent selected from hydrogen and alkyl groups containing between 1 and about 10 carbon atoms; $R^2$ is a substituent selected from aliphatic, alicyclic and aromatic radicals containing between 1 and about 12 carbon atoms and 0-3 oxygen or nitrogen atoms; and $R^1$ and $R^2$ when taken together with connecting elements form an alicyclic structure.

4. A smoking composition in accordance with claim 3 wherein the substituted-pyrazine compound is 2-(2-hydroxy-2-phenylethyl)-3,5,6-trimethylpyrazine.

5. A smoking composition in accordance with claim 3 wherein the substituted-pyrazine compound is 2-(2-hydroxy-2-p-methylphenylethyl)-3,5,6-trimethylpyrazine.

6. The smoking composition in accordance with claim 3 wherein the substituted-pyrazine compound is 2-(2-hydroxy-2-p-methoxyphenylethyl)-3,5,6-trimethylpyrazine.

7. The smoking composition in accordance with claim 3 wherein the substituted-pyrazine compound is 2-[2-hydroxy-2-(2-furyl)ethyl]-3,5,6-trimethylpyrazine.

8. A smoking composition in accordance with claim 3 wherein the substituted-pyrazine compound is 2-(2-hydroxy-4-methylphentyl)-3,5,6-trimethylpyrazine.

9. A smoking composition in accordance with claim 3 wherein the substituted-pyrazine compound is 2-(2-hydroxy-2-methyl-3-oxobutyl)-3,5,6-trimethylpyrazine.

10. A smoking composition in accordance with claim 3 wherein the substituted-pyrazine compound is 2,3-dihydroxy-2,3-dimethyl-1,4-bis(3,5,6-trimethyl-2-pyrazyl)butane.

11. A smoking composition in accordance with claim 3 wherein the substituted-pyrazine compound is 2-(2-hydroxy-2-p-methoxyphenylethyl)-6-methylpyrazine.

12. A smoking composition in accordance with claim 3 wherein the substituted-pyrazine compound is 2-(2-hydroxy-2-p-methoxyphenylethyl)-3-methylpyrazine.

13. A smoking composition in accordance with claim 3 wherein the substituted-pyrazine compound is 2-(2-hydroxy-2-p-methoxyphenylethyl)-5-methylpyrazine.

14. A smoking composition in accordance with claim 3 wherein the substituted-pyrazine compound is 2,3-dihydroxy-2,3-dimethyl-1-(3,5,6-trimethyl-2-pyrazyl)-4-(6-methyl-2-pyrazyl)butane.

15. A smoking composition in accordance with claim 3 wherein the substituted-pyrazine compound is 1-methyl-3-hydroxy-3-(3,5,6-trimethyl-2-pyrazyl)methyl-4-isopropylcyclohexane.

16. A smoking composition in accordance with claim 3 wherein the substituted-pyrazine compound is 2-[2-hydroxy-2-(2-pyrazyl)proypl]-3,5,6-trimethylpyrazine.

17. A smoking composition in accordance with claim 3 wherein the substituted-pyrazine compound is 2-(2-hydroxy-2-methylheptyl)-3,5,6-trimethylpyrazine.

18. A smoking composition comprising an admixture of (1) combustible filler selected from the group consisting of natural tobacco, reconstituted tobacco and non-tobacco substitutes, and (2) betweetn about 0.0005 and 2 weight percent, based on the total weight of filler of a substituted-pyridine compound corresponding to the formula:

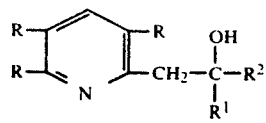

wherein R is a substituent selected from hydrogen and methyl; R¹ is a substituent selected from hydrogen and alkyl groups containing between 1 and about 10 carbon atoms; R² is a substituent selected from aliphatic, alicyclic and aromatic radicals containing between 1 and about 12 carbon atoms and 0-3 oxygen or nitrogen atoms; and R¹ and R² when taken together with connecting elements form an alicyclic structure.

19. A smoking composition in accordance with claim 18 wherein the substituted-pyridine compound is 2-(2-hydroxy-2-phenylethyl)pyridine.

20. A smoking composition in accordance with claim 18 wherein the substituted-pyridine compound is 2-(2-hydroxy-2-p-methoxyphenylethyl)pyridine.

21. A smoking composition in accordance with claim 18 wherein the substituted-pyridine compound is 2-(2-hydroxy-2-phenylethyl)-6-methylpyridine.

22. A smoking composition comprising an admixture of (1) combustible filler selected from the group consisting of natural tobacco, reconstituted tobacco and non-tobacco substitutes, and (2) between about 0.0005 and 2 weight percent based on the total weight of filler, of a substituted-pyridine compound corresponding to the formula:

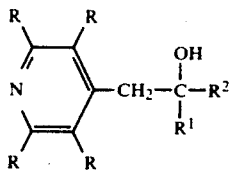

wherein R is a substituent selected from hydrogen and methyl; R¹ is a substituent selected from hydrogen and alkyl groups containing between 1 and about 10 carbon atoms; R² is a substituent selected from aliphatic, alicyclic and aromatic radicals containing between 1 and about 12 carbon atoms and 0-3 oxygen or nitrogen atoms; and R¹ and R² when taken together with connecting elements form an alicyclic structure.

23. A smoking composition in accordance with claim 22 wherein the substituted-pyridine compound is 4-(2-hydroxy-2-phenylethyl)pyridine.

24. A method of preparing a smoking composition which is adapted to impart flavoring to the mainstream and sidestream smoke under smoking conditions, which method comprises incorporating into natural tobacco, reconstituted tobacco or non-tobacco substitute between about 0.0005 and 2 weight percent, based on composition weight, of a flavorant additive corresponding to the formula:

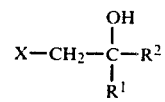

wherein X is selected from pyrazine and pyridine radicals corresponding to the chemical structures:

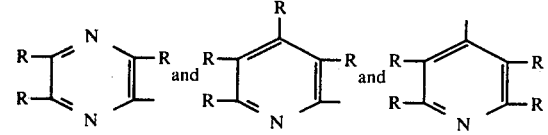

wherein R is a substituent selected from hydrogen and methyl; R¹ is a substituent selected from hydrogen and alkyl groups containing between 1 and about 10 carbon atoms; R² is a substituent selected from aliphatic, alicyclic and aromatic groups containing between 1 and about 12 carbon atoms, and any heteroatom present in the R² group is either oxygen or nitrogen; and R¹ and R² were taken together with connecting elements form an alicyclic structure.

25. A method of improving the aroma imparted by the burning of a combustible article of manufacture within the environment of a human habitat, which method comprises incorporating into said article of manufacture prior to its combustion between about 0.01 and 10 weight percent, based on the weight of combustible content, of a substituted heterocyclic compound corresponding to the formula:

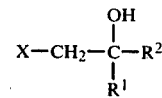

wherein X is selected from pyrazine and pyridine radicals corresponding to the chemical structures:

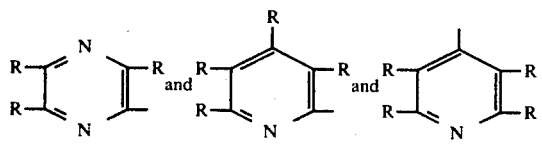

wherein R is a substituent selected from hydrogen and methyl; R¹ is a substituent selected from hydrogen and alkyl groups containing between 1 and about 10 carbon atoms; R² is a substituent selected from aliphatic, alicyclic and aromatic groups containing between 1 and about 12 carbon atoms, and any heteroatom present in the R² group is either oxygen or nitrogen; and R¹ and R² when taken together with connecting elements form an alicyclic structure.

* * * * *

UNITED STATES PATENT AND TRADEMARK OFFICE
CERTIFICATE OF CORRECTION

PATENT NO. : 4,259,969
DATED : April 7, 1981
INVENTOR(S) : Yoram Houminer et al

It is certified that error appears in the above—identified patent and that said Letters Patent is hereby corrected as shown below:

Column 15, lines 28 and 31, replace "filter" by --filler--.

Column 16, line 33, replace "methylphentyl" by --methylpentyl--.

Column 16, line 60, replace "proypl" by --propyl--.

Column 16, line 67, replace "betweetn" by --between--.

Column 18, line 25, replace "were" by --when--.

Signed and Sealed this

Twenty-fifth Day of May 1982

[SEAL]

Attest:

GERALD J. MOSSINGHOFF

Attesting Officer

Commissioner of Patents and Trademarks